United States Patent
Codd et al.

(10) Patent No.: US 11,439,461 B2
(45) Date of Patent: Sep. 13, 2022

(54) AUTOMATED SURGICAL ROBOT

(71) Applicant: Duke University, Durham, NC (US)

(72) Inventors: Patrick Codd, Durham, NC (US);
Kimberly Hoang, Durham, NC (US);
David Britton, Durham, NC (US);
Westin Hill, Durham, NC (US);
Weston Ross, Durham, NC (US)

(73) Assignee: Duke University, Durham, NC (US)

( * ) Notice: Subject to any disclaimer, the term of this patent is extended or adjusted under 35 U.S.C. 154(b) by 361 days.

(21) Appl. No.: 16/486,942

(22) PCT Filed: Feb. 20, 2018

(86) PCT No.: PCT/US2018/018838
§ 371 (c)(1),
(2) Date: Aug. 19, 2019

(87) PCT Pub. No.: WO2018/152538
PCT Pub. Date: Aug. 23, 2018

(65) Prior Publication Data
US 2021/0128236 A1    May 6, 2021

Related U.S. Application Data

(60) Provisional application No. 62/623,159, filed on Jan. 29, 2018, provisional application No. 62/622,452, (Continued)

(51) Int. Cl.
*A61B 18/20* (2006.01)
*G16H 20/40* (2018.01)
(Continued)

(52) U.S. Cl.
CPC .............. *A61B 18/20* (2013.01); *A61B 34/25* (2016.02); *G16H 20/40* (2018.01); *G16H 30/40* (2018.01);
(Continued)

(58) Field of Classification Search
CPC .................. A61B 18/20; A61B 34/25; A61B 2017/00057; A61B 2018/2025;
(Continued)

(56) References Cited

U.S. PATENT DOCUMENTS

| | | |
|---|---|---|
| 5,049,147 A | 9/1991 | Danon |
| 5,617,645 A | 4/1997 | Wick et al. |

(Continued)

OTHER PUBLICATIONS

Authorized Officer: Lee W. Young, International Search Report and Written Opinion issued in PCT application No. PCT/US2018/018838, dated May 7, 2018, 14 pp.

(Continued)

*Primary Examiner* — John R Downey
(74) *Attorney, Agent, or Firm* — Kaplan Breyer Schwarz, LLP

(57) ABSTRACT

An automated laser-surgery system for performing a closed-loop surgical procedure is disclosed. The procedure includes forming a post-procedural goal based on a three-dimensional (3D) image of a surgical site, planning a path for a surgical laser signal based on the post-procedural goal, performing a procedural pass by steering the surgical laser signal along the path, measuring the surface of the surgical site after the procedural pass, updating a model based on the measured effect at the surgical site, and evaluating the success of the procedural pass based on the surface measurement and the post-procedural goal. If necessary, a new path is planned based on the post-procedural goal and the surface measurement a new pass based on that path is performed, and the surface is again measured to evaluate the success of the new pass. These operations are repeated as a closed-loop sequence as many times as necessary to achieve success.

22 Claims, 8 Drawing Sheets

Related U.S. Application Data filed on Jan. 26, 2018, provisional application No. 62/460,966, filed on Feb. 20, 2017.

(51) Int. Cl.
| | |
|---|---|
| *G16H 50/50* | (2018.01) |
| *G16H 50/70* | (2018.01) |
| *G16H 30/40* | (2018.01) |
| *G16H 40/63* | (2018.01) |
| *A61B 17/00* | (2006.01) |
| *A61B 34/00* | (2016.01) |
| *A61B 34/10* | (2016.01) |
| *A61B 34/32* | (2016.01) |

(52) U.S. Cl.
CPC ............. *G16H 40/63* (2018.01); *G16H 50/50* (2018.01); *G16H 50/70* (2018.01); *A61B 34/32* (2016.02); *A61B 2017/00057* (2013.01); *A61B 2018/2025* (2013.01); *A61B 2018/205547* (2017.05); *A61B 2034/104* (2016.02); *A61B 2034/105* (2016.02)

(58) Field of Classification Search
CPC .. A61B 2018/205547; A61B 2034/104; A61B 2034/105; G16H 20/40; G16H 30/40; G16H 40/63; G16H 50/50; G16H 50/70
USPC .......................................................... 606/4–6
See application file for complete search history.

(56) References Cited

U.S. PATENT DOCUMENTS

| | | | |
|---|---|---|---|
| 5,867,297 | A | 2/1999 | Kiang et al. |
| 6,706,035 | B2 | 3/2004 | Cense et al. |
| 6,984,228 | B2 | 1/2006 | Anderson et al. |
| 8,652,061 | B2 | 2/2014 | Yu et al. |
| 2002/0183811 | A1 | 12/2002 | Irwin |
| 2008/0058782 | A1 | 3/2008 | Frangineas et al. |
| 2010/0114077 | A1* | 5/2010 | Dai ................. A61F 9/00806 606/5 |
| 2010/0256965 | A1 | 10/2010 | Rathjen |
| 2011/0028951 | A1* | 2/2011 | Raksi .................. A61F 9/0084 606/4 |
| 2011/0040295 | A1* | 2/2011 | Pierce .................. A61N 5/0613 606/11 |
| 2011/0184395 | A1* | 7/2011 | Schuele .................. A61F 9/008 606/5 |
| 2011/0224657 | A1* | 9/2011 | Stevens .................... A61F 9/008 606/5 |
| 2011/0282331 | A1* | 11/2011 | Brennan ............ G01B 9/02028 606/4 |
| 2011/0319877 | A1 | 12/2011 | Anderson |
| 2012/0059441 | A1 | 3/2012 | Chang et al. |
| 2013/0158530 | A1 | 6/2013 | Goldshleger et al. |
| 2013/0184693 | A1 | 7/2013 | Neev |
| 2014/0128853 | A1* | 5/2014 | Angeley ............. A61F 9/00827 606/4 |
| 2015/0327930 | A1 | 11/2015 | Bruno et al. |
| 2016/0158575 | A1 | 6/2016 | Levatter |
| 2019/0175272 | A1* | 6/2019 | Khan ..................... A61B 34/32 |

OTHER PUBLICATIONS

Hongen Liao et al., "An integrated diagnosis and therapeutic system using intra-operative 5-aminolevulinic-acid-induced fluorescence guided robotic laser ablation for precision neurosurgery", "Medical Image Analysis", Nov. 28, 2010, Publisher: Elsevier B.V., doi:10.1016/j.media.2010.11.004, pp. 754-766, vol. 16 (2012).

Hongen Liao et al., "Automatic laser scanning ablation system for high-precision treatment of brain tumors", "Lasers in Medical Science", Aug. 4, 2012, Publisher: Springer-Verlag London Ltd, DOI 10.1007/s10103-012-1164-6, pp. 891-900, vol. 28.

Yingwei Fan et al., "A novel integration of spectral-domain optical-coherence-tomography and laswer-ablation system for precision treatment", "International Journal of Computer Assisted Radiology and Surgery", Sep. 9, 2017, DOI 10.1007/s11548-017-1664-8, 13 pp.

Yingwei Fan, "Optical coherence tomography for precision brain imaging, neurosurgical guidance and minimally invasive theranotics", "BioScience Trends" Advance Publication, Jan. 15, 2018, DOI: 10.5582/bst.2017.01258, pp. P1-P12.

Authorized Officer Lee W. Young, International Search Report and Written Opinion dated Sep. 19, 2019 issued in PCT Patent Application PCT/IB2018/056284.

* cited by examiner

AUTOMATED SURGICAL ROBOT

STATEMENT OF RELATED CASES

This case claims priority to U.S. Provisional Patent Application Ser. No. 62/460,966 filed on Feb. 20, 2017, U.S. Provisional Patent Application Ser. No. 62/622,452 filed on Jan. 26, 2018, U.S. Provisional Patent Application Ser. No. 62/623,159 filed on Jan. 29, 2018, each of which is incorporated herein by reference.

TECHNICAL FIELD

The present disclosure relates to surgical systems in general, and, more particularly, to robotic surgery.

BACKGROUND

Laser surgery has become a critical procedure in the treatment of many conditions, such as brain cancer, skin cancer, and urinary-tract conditions, among others. In addition, laser surgery has been directed to the treatment of many non-life-threatening ailments, such as tattoo removal and the like.

Unfortunately, in many instances, a life-threatening condition is deemed inoperable because its surgical treatment is beyond the ability of even state-of-the-art laser treatments. Furthermore, some procedures require a greater accuracy or precision than is possible within the limitations of the human hand and physiologic tremor, such as dissecting a tumor from a cranial nerve or critical vascular structure, removing a tumor from a highly eloquent or functional brain tissue that controls a delicate function, or manipulating tissue on the brainstem.

Operability, extent of resection, and complication rates are inexorably linked to limitations in current surgical procedures and medical imaging that can be applied. For example, brain tumors can be treated by resecting the cancerous tissue using a hand-held laser tool, which is often invisible to the human eye. For even the most-skilled surgeons, such an approach taxes their ability to controllably manipulate tissue where desired without impacting tissue that should not be disturbed. As a result, such procedures introduce the risk of inadvertent delivery of injury to delicate neurovascular tissues with risk of neurologic injury or death.

While robotic-assisted surgery has become relatively commonplace in other realms of surgery, it is not currently widely used in neurosurgery; however, the demands and limitations of current practice might be addressed through its implementation. To date, the robotic applications in clinical neurosurgery have largely been limited to improving the positional accuracy during stereotaxy or the positioning of optical devices for use in surgery. Neurosurgeons continue to rely on mechanical dissection where instruments including the bipolar electrocautery, suction, and probe dissector are used to manipulate sensitive neurologic structures under direct visualization; consequently, the precision of these tools continues to be limited to that of their human operator. While incremental improvements in patient outcomes can be realized by refining neurosurgical techniques, more meaningful advances must be achieved through advancing robotic assistance and imaging in the operating room.

In addition, there is a fundamental cognitive-flow limitation as ever increasing modalities for imaging, intra-procedural monitoring, and multispectral data recordings are integrated into care but are not fully utilized in the surgical setting, since integrating such vast quantities of information in real time by a single surgeon/operator, or even an entire care team, is difficult, if not impossible.

Furthermore, even with the advanced level of robotic assistance currently available in the operating room, a surgeon cannot perform at the desired level of precision while constrained by a timeframe so heavily weighted by cost. Some of the basic surgical decisions must be yielded to the assisting robot, thereby giving it a higher level of automation than previously demonstrated in commercially available surgical robots.

A laser-surgery approach that reduces the rate of complication, decreases the percentage of conditions deemed inoperable, increases accuracy and precision of intervention, and/or reduces operating-room time and cost would be a welcome advance in the state of the art

SUMMARY

Embodiments of the present disclosure enable automated surgical procedures without some of the costs and disadvantages of the prior art. Systems and methods in accordance with the present disclosure employ a laser signal to manipulate tissue at a surgical site, where the path of the laser signal, as well as its orientation, power and speed, are automatically controlled based on a pre-procedural model and a post-procedural goal. After a procedural pass of the surgical procedure has been performed at the surgical site, an intra-procedural assessment of the results of that pass is performed to determine how accurately the post-procedural goal has been achieved. In cases where additional tissue manipulation is warranted, a path for another pass of the laser through the surgical site is planned and performed via the automated surgical system. The planning of the surgical path, the execution of a procedural pass based on the planned path, and the performance of an intra-procedural assessment of that pass based on the post-procedural goal collectively define a "closed-loop" sequence that can be repeated as many times as needed to realize the desired surgical outcome. Furthermore, in some embodiments, its implementation enables real-time adaptation of the surgical procedure based on the actual response to the tissue at a surgical site to the surgical laser signal. Some embodiments of the present disclosure are particularly well-suited for use in applications in neurosurgery (e.g., brain surgery, etc.), dermatology (e.g., tattoo removal, treatment of skin cancers, etc.), and eye surgery, among others.

An illustrative embodiment is an automated surgical system comprising a processing circuit, a surgical laser, a two-axis beam scanner, and a surface profiler, where the processing circuit plans a path for a first pass of a surgical laser signal through a surgical site based on a pre-procedural three-dimensional image of the field, an intra-procedural image of the field, and the desired surgical outcome. The processing circuit executes a procedural pass by controlling the beam scanner to steer the surgical laser signal over the desired path while simultaneously controlling one or more of its characteristics (e.g., power, beam shape, focus, focal depth, spot size, trajectory, etc.). The surface profiler performs an intra-procedural surface analysis of the surgical site and provides it to the processing circuit as real-time feedback on the effectiveness of the first pass relative to the desired outcome of the surgical procedure. If the result of the first pass does not satisfy the desired outcome, a second pass of the surgical laser signal through the surgical site is planned and performed, and the results relative to the desired outcome are assessed. In some embodiments, the second pass is planned based on a model derived from the measured response of the tissue at the surgical site to the first pass of the surgical laser signal.

In the illustrative embodiment, the surface profiler is a laser triangulation sensor whose interrogation signal is provided to the beam scanner, which directs it over the surgical site. A portion of the interrogation signal is reflected from the surgical site and provided back to the laser triangulation sensor via the beam scanner. A determination of the range (i.e., depth) for each of a plurality of points along the path is achieved by correlating the instantaneous output of the laser triangulation sensor, the instantaneous reflected signal received at the triangulation sensor, and the instantaneous position of the beam scanner at each point. In some embodiments, the interrogation signal is combined with the surgical laser signal to form a single composite beam that is scanned over the surgical site by the beam scanner.

In some embodiments, a guidance signal comprising visible light is combined with the surgical laser signal to enable a surgeon to easily monitor the position of the surgical laser signal during a procedure in real time.

In some embodiments, one or more of a variety of types of surface profilers, such as an interferometer, optical coherence tomography (OCT) device, high-resolution visible light stereo-vision imaging system ultrasound imaging system, etc., are used to determine the range for each of the plurality of points in the surgical site. In some embodiments, one or more additional feedback modalities (e.g., other topological sensors, video imaging, multi-spectral imaging, optical coherence tomography, magnetic resonance imaging (MRI), computed tomography (CT), etc.) are used to evaluate the intra-procedural and post-procedural condition of the surgical site.

In some embodiments, automated surgical path planning is employed to generate the desired path of the surgical laser signal through the surgical site. In some of these embodiments, automated path planning includes generating an estimate of the tissue parameters at the surgical site by creating a test feature, analyzing the surface of the test feature to form a topological map of its structure, and creating a model of the reaction of the tissue to the surgical laser signal based on this topological map. In some embodiments, a measured response of the tissue at the surgical site to a previous pass of the surgical laser is used to create or update a model of the reaction of the tissue for use in a subsequent pass.

In some embodiments, validation of the intended surgical path by a surgeon is required before execution of a procedural pass is enabled.

An embodiment in accordance with the present disclosure is a surgical system for manipulating tissue at a surgical site, the system comprising: a first laser operative for providing a first laser signal, the first laser signal being operative for manipulating tissue at the surgical site; a beam scanner that is configured to controllably direct the first laser signal to points within a first region of the surgical site; a surface profiler that is configured to measure a range for points within the first region; and a processing circuit that is configured to: (1) plan a first path for the first laser signal within the first region, wherein the first path is based on a post-procedural goal; (2) control the first laser signal along the first path; (3) generate a first intra-procedural model of the surgical site based on a measured range for each of a first plurality of points within the first region, wherein the range for each point of the first plurality thereof is measured after the first laser signal has traversed the first path; and (4) perform a first comparison of the post-procedural goal and the first intra-procedural model.

Another embodiment in accordance with the present disclosure is a method comprising: planning a first path for the first laser signal within a first region of a surgical site, wherein the first path is based on a post-procedural goal; controlling the first laser signal along the first path; generating a first intra-procedural model of the surgical site based on a measured range for each of a first plurality of points within the first region, wherein the range for each point of the first plurality thereof is measured after the first laser signal has traversed the first path; and performing a first comparison of the post-procedural goal and the second intra-procedural model.

DETAILED DESCRIPTION

Figure 1:
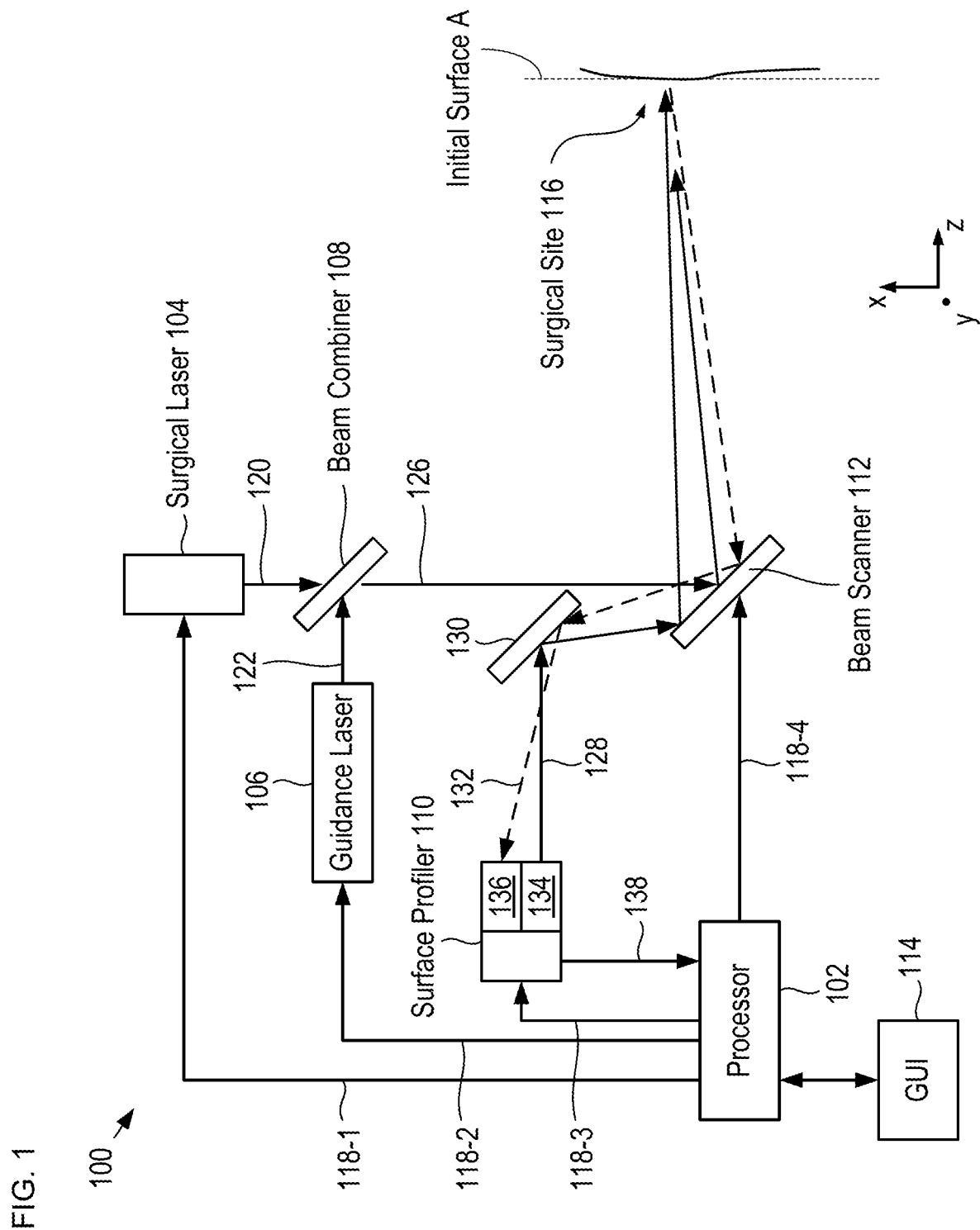
FIG. 1 depicts a schematic drawing of an illustrative embodiment of an automated surgical system in accordance with aspects of the present disclosure.

FIG. 1 depicts a schematic drawing of an illustrative embodiment of an automated surgical system in accordance with aspects of the present disclosure. System 100 is a laser-surgery system operative for manipulating tissue at a surgical site. For the purposes of this Specification, including the appended claims, the term "tissue manipulation" is defined as interacting with a tissue to effect a change, such as ablation, inducing necrosis in the tissue, inducing a chemical change to an ink or other foreign substance in the tissue, inducing coagulation, cutting, heating, illuminating, disrupting, and the like. Furthermore, the term "surgical," as used herein, is intended to include any surgical or non-surgical medical procedure that can be performed within or outside of an operating room.

System 100 includes processing circuit 102, surgical laser 104, guidance laser 106, beam combiner 108, surface profiler 110, beam scanner 112, and graphical user interface 114. In the depicted example, system 100 is specifically configured to controllably ablate soft brain matter along a desired surgical path at surgical site 116. Although the illustrative embodiment is a laser-surgery system configured to resect brain tumors via ablation, some systems in accordance with the present disclosure are well suited for use in other medical procedures, such as tattoo removal via laser-induced chemical breakdown of tattoo inks, laser-induced thermal necrosis for treatment of skin-cancer cells, removal of other soft pathological tissues, coagulation or ablation of vascular lesions and vascular structures, removal of both benign and malignant tissues, among others.

Processing circuit 102 comprises processing circuitry, control circuitry, memory, and the like, and is configured to, among other things, provide control signals 118-1, 118-2, 118-3, and 118-4 to surgical laser 104, guidance laser 106, surface profiler 110, and beam scanner 112, respectively, receive measurement data from surface profiler 110, generate a desired path through surgical site 116 for surgical laser signal 120, store one or more pre-generated three-dimensional (3D) maps of surgical site 116, utilize and tune a tissue manipulation model simulator, and generate an assessment of the success of a surgical procedure based on a comparison of the measurement data received from surface profiler and a stored 3D map of the surgical site. In the embodiment of FIG. 1, the processing circuit is implemented as a single, discrete component within system 100. In various other embodiments, the processing circuit can be distributed, at least in part, among multiple components of system 100, implemented, in part or in full, in a remote or cloud-based computing system, or otherwise implemented in a suitable arrangement for carrying out the functions described herein.

Surgical laser 104 is a conventional carbon-dioxide ($CO_2$) surgical laser, which provides laser signal 120 to beam combiner 108. Laser signal 120 has a wavelength of approximately 10.6 microns and is operative for ablating biological material to perform tissue resection. In some embodiments, surgical laser 104 is a different laser, such as a neodymium-doped yttrium aluminum garnet (Nd:YAG) laser, a Q-switched laser suitable for removal of tattoo ink, a pulsed-dye laser for treating basal cell carcinoma, and the like. The choice of source for surgical laser 104 is based on several factors, such as intended application, the material properties of the tissue to be manipulated, location of the tissue to be manipulated. Myriad lasers can be used in surgical laser 104 without departing from the scope of the present disclosure.

Guidance laser 106 is a conventional visible-light laser, which provides laser signal 122. In the depicted example, guidance laser 106 is a helium-neon laser that emits red light having a wavelength of approximately 632.8 nm; however, any laser that emits light at a visible wavelength can be used in guidance laser 106. In some embodiments, guidance laser 106 is not included.

Beam combiner 108 is a conventional dichroic beam splitter that receives laser signal 120 from surgical laser 104 and laser signal 122 from guidance laser 106 and combines them into composite light signal 126. The addition of a visible-light signal to the surgical laser signal provides a visual indicator of where surgical laser signal 120 is incident on surgical site 116, thereby enabling a surgeon (or other user) to visually monitor the progress of the surgical procedure and intercede, if desired.

Surface profiler 110 is a conventional laser triangulation sensor suitable for determining the range (position along the z-direction) of points within surgical site 116. Surface profiler 110 includes solid-state laser light source 134 and detector array 136 (typically a CMOS/CCD detector array). Light source 134 provides interrogation signal 128, which is directed to surgical site 116 via conventional mirror 130 and beam scanner 112. A portion of interrogation signal 128 is reflected back from surgical site 116 as reflected signal 132, which is directed to surface profiler 110 via beam scanner 112 and mirror 130 and focused onto detector array 136 via suitable focusing optics. The position at which reflected signal 132 strikes the detector array is a function of the range (i.e., depth) of the point on surgical site 116 on which interrogation signal 128 is incident. As the tissue at this point is ablated, the range at the point increases and the position of reflected signal 132 on the detector array shifts commensurately.

In the depicted example, interrogation signal 128 has a wavelength of approximately 670 nm; however, myriad wavelengths can be used for interrogation signal 128.

In some embodiments, all of laser signals 120 and 122 and interrogation signal 128 are combined into a single composite laser signal via conventional beam combiners.

Beam scanner 112 is a conventional two-axis scanning-mirror system for steering composite signal 126 and interrogation signal 128 in two dimensions. In the depicted example, beam scanner 112 is a two-axis galvanometer mirror system; however, there are many two-axis beam steering systems suitable for use in beam scanner 112. Beam scanners suitable for use in embodiments in accordance with the present disclosure include, without limitation, two-axis gimbal-mounted mirrors, pairs of single-axis turning mirrors, MEMS beam-steering mirrors, and the like.

In use, the beam-scanner is positioned in close proximity to the surgical site, while bulky laser sources, processing circuits, computing systems, etc. can be located remotely. This mitigates sterilization issues and improves the visibility of the surgical site for the surgeon.

Graphical User Interface (GUI) 114 is a hardware and/or software system that enables a user, such as a surgeon, to interact with path-planning software routines executed by processing circuit 102. GUI 114 is configured to enable the user to specify a classification for at least one region within a 3D model of the surgical site, such as classifying tissue in a region for special consideration (e.g., removal, protection, and the like).

It should be noted that system 100 can also include various optical elements for manipulating and/or shaping light signals, such as collimating optics, focusing optics, spatial and spectral filtering optics, and the like.

Figure 2:
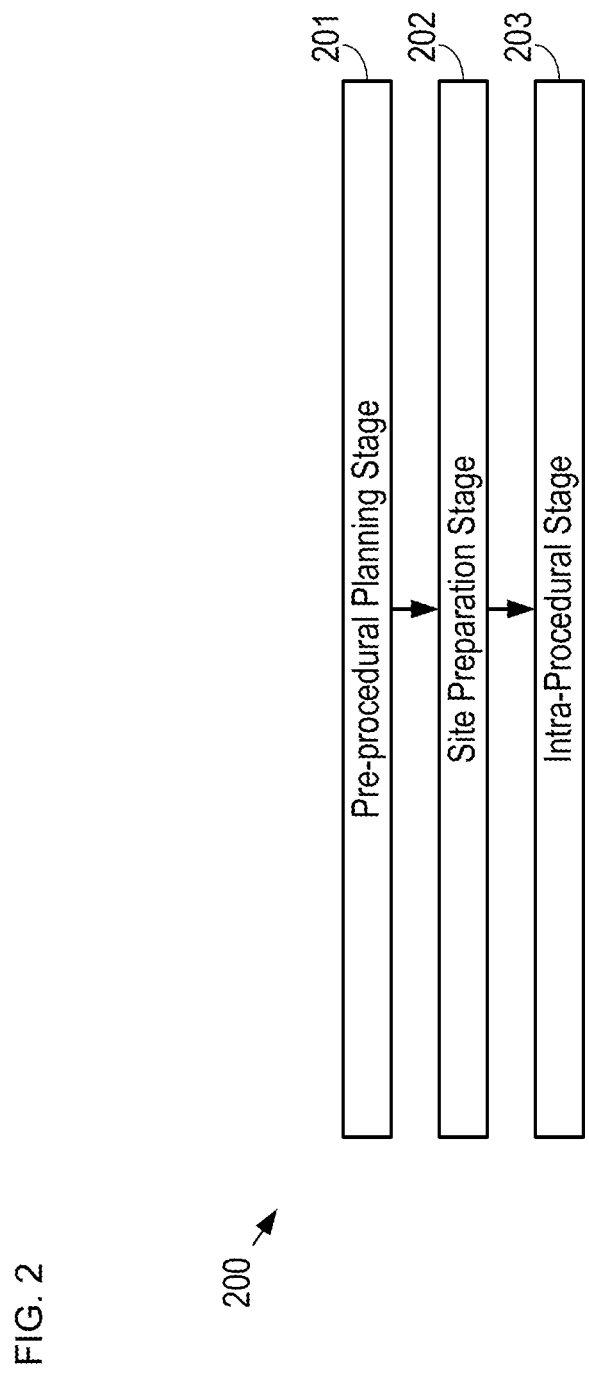
FIG. 2 depicts the stages of an exemplary automated laser surgery method in accordance with the illustrative embodiment.

FIG. 2 depicts the stages of an exemplary automated laser surgery method in accordance with the illustrative embodiment. Method 200 can be implemented using system 100 of FIG. 1, and reference is made thereto in following description of FIGS. 2-8B for the sake of clarity. However, other systems suitable for implementation of method 200 are also contemplated by the present disclosure. Method 200 is a surgery method suitable for resection of a brain tumor and includes three stages: pre-procedural planning stage 201, in which a post-procedural goal for surgical site 116 is developed; site preparation stage 202, in which surgical site 116 is prepared for surgery and system 100 is aligned relative to the surgical site to enable the desired procedure; and intra-procedural stage 203, in which one or more procedural passes of the surgical laser signal through the surgical site are performed and, after each pass, the surgical site is analyzed to determine whether the post-procedural goal has been achieved. Each stage of method 200 includes a series of operations, as discussed below.

Pre-procedural stage 201 includes a set of operations that enable the development of a computer model representative of the desired outcome of a surgical procedure.

Figure 3:
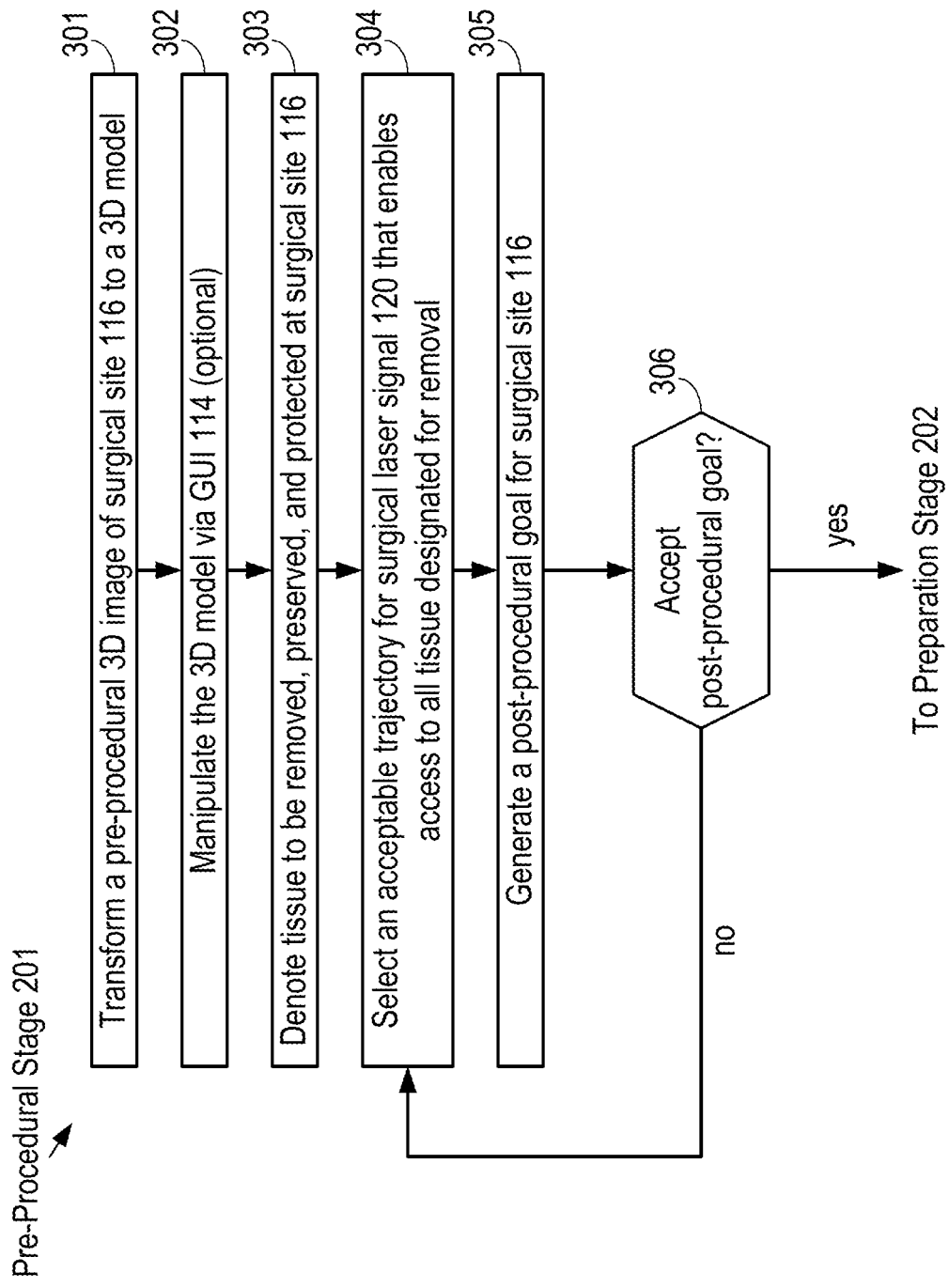
FIG. 3 depicts an exemplary implementation of a pre-procedural stage in accordance with the illustrative embodiment.

FIG. 3 depicts an exemplary implementation of a pre-procedural stage in accordance with the illustrative embodiment. Pre-procedural stage 201 begins with operation 301, wherein a pre-procedural 3D image of surgical site 116 is transformed into a 3D model by processing circuit 102. For the purposes of this Specification, including the appended claims, the term "pre-procedural" is defined as referring to an operation performed before the surgical site is prepared for surgery. For example, a pre-procedural image is an image taken of a surgical site before the site has been exposed (e.g., via removal of a portion of a skull, etc.) and prepared for surgery. After pre-procedural stage 201, therefore, some change in the state of the surgical site might be expected due to site preparation.

In the depicted example, the 3D model is based on a pre-procedural image of surgical site 116, which is generated using magnetic resonance imaging (MRI). In some embodiments, a different conventional imaging modality is used to create a pre-procedural 3D image of the surgical site. Examples of alternative imaging modalities suitable for use in embodiments in accordance with the present disclosure include, without limitation, computed tomography (CT), optical coherence tomography (OCT), x-ray imaging, ultrasound, spectroscopy, microscopy, endoscopy, visible light camera, and the like.

At optional operation 302, the 3D model is manipulated by a user (e.g., a surgeon, etc.) through GUI 114. This manipulation can include, for example, identification of important anatomical features in the model, such as blood vessels, nerves, etc., delineation of critical functional regions within the surgical site, such as speech, motor function, sensory function, etc. that are to be protected from damage during a surgical procedure, confirmation or correction of computer generated mapping of the surgical site and boundaries, and the like. It should be noted that functional imaging, such as functional MRI, magnetoencephalography, electroencephalography, and the like, is sometimes used to identify functional areas with the surgical site.

At operation 303, the surgeon employs GUI 112 to specify classifications for one or more tissue regions within surgical site 116. Such tissue classifications include, without limitation, tissue to be manipulated at the surgical site; tissue to be removed at the surgical site; tissue that should remain after surgery; tissue that should not be disturbed during the surgical procedure; healthy tissue that can be removed, if necessary, to access tissue designated for removal, to provide a safety margin, etc.; and the like.

At operation 304, a trajectory for surgical laser signal 120 is selected for each region of tissue to be removed, where the trajectory is based on the tissue identification performed in operation 303. In some cases, more than one trajectory is required at one or more regions in the surgical site in order to effectively remove unwanted tissue. The trajectory is defined as both a function of the location of the distal end of the beam scanner 112 relative to the surgical site 116 and also the position of the beam scanner actuators (e.g. mirrors).

At operation 305, processing circuit 102 generates a post-procedural goal that is a three-dimensional model of the desired state of surgical site 116 after the surgical procedure is complete.

At operation 306, the user accepts or rejects the post-procedural goal. It should be noted that, typically, the user has the opportunity to modify the post-procedural goal at virtually any point in method 200.

If the goal is rejected, pre-procedural stage 201 returns to operation 304 where a different trajectory is selected for at least one portion of surgical site 116. Using the different trajectory or trajectories, operations 305 and 306 are repeated and a new post-procedural goal is generated and evaluated.

Once an acceptable post-procedural goal is generated, method 200 continues with site preparation stage 202.

Figure 4:
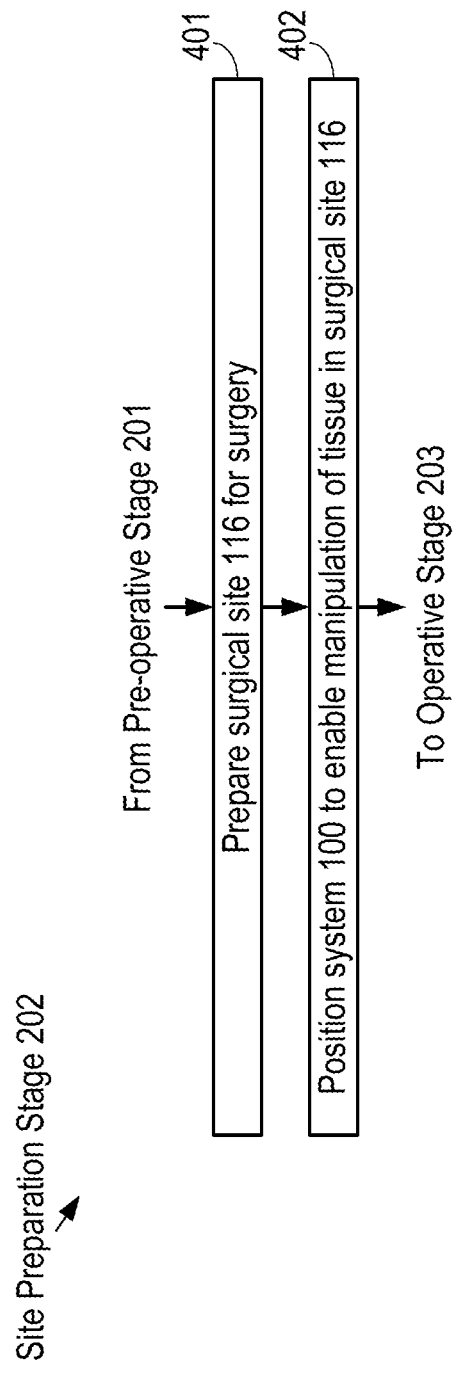
FIG. 4 depicts an exemplary implementation of a preparation stage in accordance with the illustrative embodiment.

FIG. 4 depicts an exemplary implementation of a preparation stage in accordance with the illustrative embodiment. Preparation stage 202 begins with operation 401, wherein surgical site 116 is prepared for surgery. In the depicted example, site preparation enabling access to the surgical site (e.g., by removing a portion of the patient's skull, making an incision, creating an access hole, etc.), removal of incidental tissue from the surgical site (e.g., opening the lining that surrounds the brain, etc.), and the like. It should be noted that, in some embodiments (e.g., dermatological applications), nothing needs to be removed to expose the surgical site for interaction with the surgical laser signal.

At operation 402, system 100 is positioned relative to surgical site to enable achievement of the post-procedural goal based on the anatomy of the patient. In some cases, system 100 must be calibrated based on input from the user and/or anatomical landmarks.

Once surgical site 116 is prepared and system 100 is in place, method 200 continues with intra-procedural stage 203.

Figure 5:
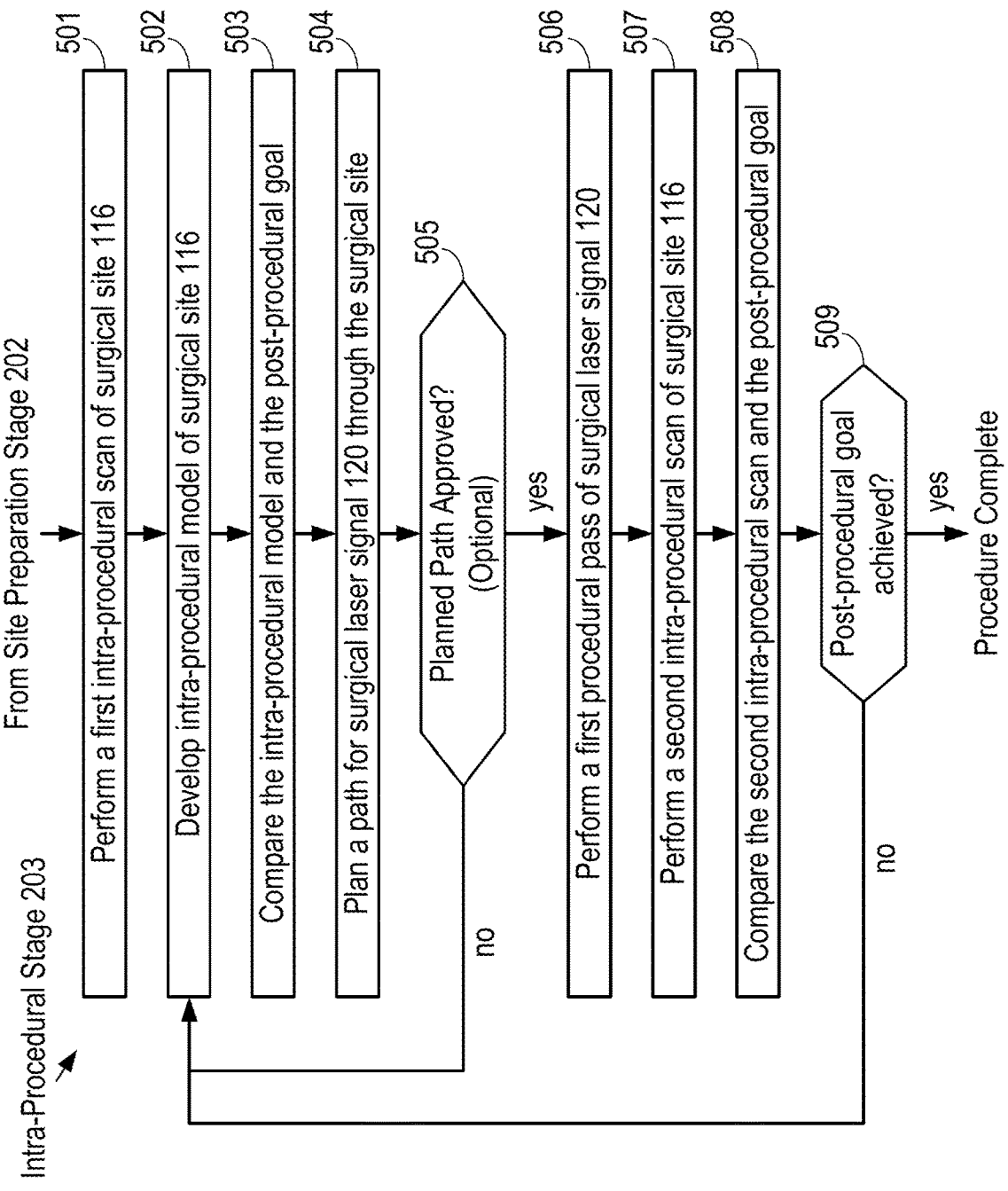
FIG. 5 depicts an exemplary implementation of an intra-procedural stage in accordance with the illustrative embodiment.

FIG. 5 depicts an exemplary implementation of an intra-procedural stage in accordance with the illustrative embodiment. Intra-procedural stage 203 begins with operation 501, wherein a first intra-procedural scan of surgical site 116 is performed. For the purposes of this Specification, including the appended claims, the term "intra-procedural" refers to an operation at a surgical site that is performed after the surgical site is prepared for surgery. In fact, typically, an intra-procedural operation is performed while the surgical site is accessible to a surgical tool, such as a surgical laser signal. For example, an intra-procedural scan is a surface scan taken of the surgical site after the site has been exposed (e.g., via removal of a portion of a skull, etc.) and prepared for surgery. An intra-procedural operation, therefore, is performed at a time after which little or no change in the state of the surgical site would be expected due to site preparation.

In the depicted example, the first intra-procedural scan of surgical site 116 is performed using the laser triangulation sensor of surface profiler 110 and beam scanner 112 to determine the range for a plurality of points within surgical site 116. To develop a surface image of surgical site 116, processing circuit 102 issues control signals 118-3 and 118-4 to surface profiler 110 and beam scanner 112, respectively, to generate interrogation signal 128 and sweep it over the plurality of points.

At each point, light is reflected back to detector array 136, through beam scanner 112 and mirror 130, as reflection signal 132. The position at which the reflection signal hits the detector array is dependent upon the range (i.e., depth into surgical site 116) of the point from which it reflects.

Processing circuit 102 receives range signal 138, which includes triangular-sensor data for each of the plurality of points. In order convert the triangular-sensor data into a range value for each point, each distance sample is correlated with the angular position of beam scanner 112 at the instant that sample was measured.

In some embodiments, an intra-procedural scan of the surgical site is performed using any of a variety of alternative imaging modalities, including, without limitation, ultrasound, CT, MRI, 3D imaging, 3D surface scanning (e.g., via a non-contact surface profiler, etc.), interferometry, conoscopic holography, visible light cameras, computer vision systems, and the like. It should be noted, however, that the use of a laser triangulation sensor affords embodiments in accordance with the present disclosure particular advantages over automated surgery systems of the prior art. For example, although an imaging modality such as intra-procedural MRI would enable full 3D image generation, it typically requires a prohibitive image-acquisition time and/or requires too large a footprint in the operating room. Furthermore, the speed at which intra-procedural MRI can image a surgical site is too typically slow for practical use.

Three-dimensional scanning using a laser triangulation sensor, however, provides a low-cost imaging method, as well as reduced intra-procedural impact while still providing an acceptable level of precision.

At operation 502, a 3D intra-procedural model of surgical site 116 is developed based on the first intra-procedural scan generated in operation 501.

At operation 503, processing circuit 102 compares the intra-procedural model to the post-procedural goal generated in operation 305 to determine any differences between them. This enables the user to intra-procedurally delineate areas of the surgical site that contain unwanted tissue while accounting for any tissue shift or deformation that might have occurred since the post-procedural goal was generated (e.g., due to the act of opening the cranial cavity thus allowing the internal volume to change, movement of a surgical site 116 relative to the system 100 due to patient movement, etc.). Thus, the intra-procedural model and pre-procedural model are aligned.

At operation 504, a desired path for surgical laser signal 120 through surgical site 116 is planned based on the differences between the intra-operative model and the post-procedural goal. The desired path includes the set of points through which surgical laser signal 120 is to pass, as well as power levels and scanning speed of the laser signal as it progresses along the desired path. A laser trajectory to achieve each point in the path on the surgical site 116 is determined by processing circuit 102 and actuated by the beam scanner 112.

In the depicted example, the desired path is determined via an automated path-planning sub-method, which calculates the path based on the post-procedural goal, the intra-procedural model, input from the surgeon via GUI 114, and an estimate of the reaction of the tissue at the surgical site to surgical laser signal 120.

Tissue response to irradiation with a known laser energy, wavelength, and power profile is a function of many tissue parameters—including, but not limited to, threshold radiant exposure, $\Phi_{th}$, tissue density, $\rho$, ablation enthalpy, $h_{abl}$, absorption coefficient, $\mu_a$, optical scattering coefficient, $\mu_s$, reduced scattering coefficient, $\mu_s'$, refractive index, n, and scattering anisotropy coefficient, g. Furthermore, a descriptive model of laser ablation or, more generally, laser manipulation of tissue, may take into account any of such parameters. In order to plan a suitable path for surgical laser signal 120 through surgical site 116, therefore, it is necessary to have an understanding of the values of these parameters. Although the path for the surgical laser signal can be planned based on generally accepted estimates of the reaction of the tissue to be manipulated, improved performance and surgical success rates are expected for surgical procedures based on tissue parameters determined for the actual surgical site.

Figure 6:
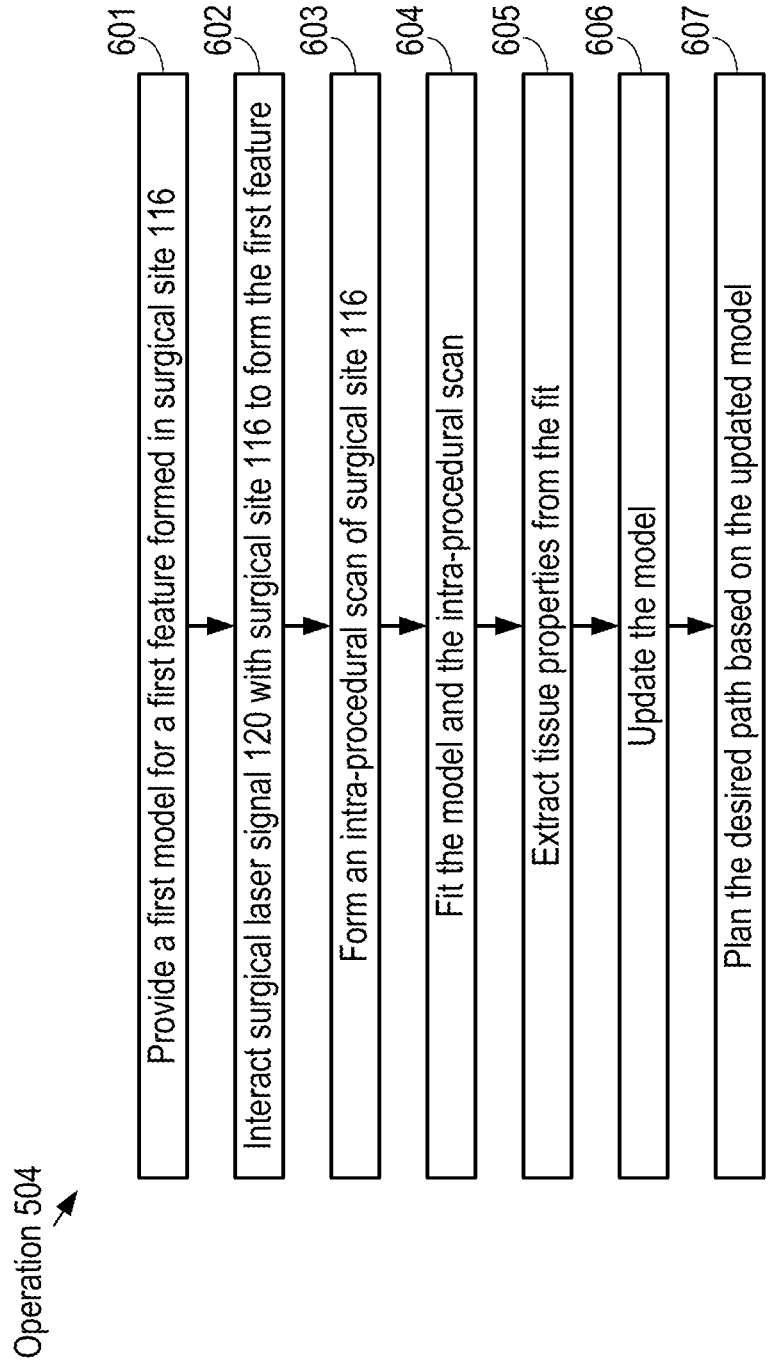
FIG. 6 depicts an exemplary sub-method suitable for estimating parameters for tissue of a surgical site and planning a desired path through the surgical site, in accordance with the illustrative embodiment.

FIG. 6 depicts an exemplary sub-method suitable for estimating parameters for tissue of a surgical site and planning a desired path through the surgical site, in accordance with the illustrative embodiment. Process 600 can be an implementation of step 504. In the depicted example, the path is planned based on a measured response of the tissue in surgical site 116 to irradiation with a known surgical laser signal. Operation 504 begins with sub-operation 601, wherein a model for a test feature formed at surgical site 116 is provided. In the depicted example, the model describes the material removed during a pass of surgical laser signal 120 through the surgical site. In some embodiments, the model is based on a different effect that can be achieved at the surgical site, such as a color change (e.g., for tattoo removal), and the like. Specifically, in the depicted example, the model predicts the surface profile of a test feature which is formed by ablating tissue while the surgery laser signal is stationary, thereby generating an ablation crater. A suitable model for an ablation crater profile can be described as:

$$\delta_{fit}(r) = A^* - \frac{dt}{\beta} E_0 e^{-2\left(\frac{r^2}{\omega_0^2}\right)}, \qquad (1)$$

where $\beta = \rho^* h_{abl}$, dt is the period of irradiation, $A^*$ is corresponds to a theoretical surface height of the tissue if the tissue radiant threshold were zero, r is the distance from the center of the beam, $E_0$ is the peak irradiance value of the beam, and $\omega_0$ is the $1/e^2$ spot size of the laser signal. This approach is based on the assumptions that the true value of the tissue radiant threshold, $\Phi_{th}$, of surgical site 116, which is not zero, can be derived from parameters fit to Equation (1) of a theoretical tissue with zero radiant threshold and that the laser signal 120 is a Gaussian beam.

It should be noted that Equation (1) includes two fitting parameters: $A^*$ and $\beta$. Subsequent calculations based on these fitting parameters allows for accurate estimation of tissue parameters pertinent to a model.

It should be noted that, while Equation (1) is one suitable model for an ablation crater, other suitable models are known and can be used in accordance with the present disclosure. Still further, a test feature can be formed using laser paths that are not stationary and therefore produce test features other than an ablation crater.

At sub-operation 602, a test feature is formed at surgical site 116 using a known power level for surgical laser signal 120.

At sub-operation 603, a cross-sectional profile of cutest feature is measured by performing an intra-procedural scan of surgical site 116 via surface profiler 110.

At sub-operation 604, the cross-sectional profile is fit to the model of the test feature (i.e., Equation (1)).

At sub-operation 605, pertinent tissue parameters are extracted from the fit. In the depicted example, the tissue parameters extracted are $\beta$ and $\Phi_{th}$.

Figure 7:
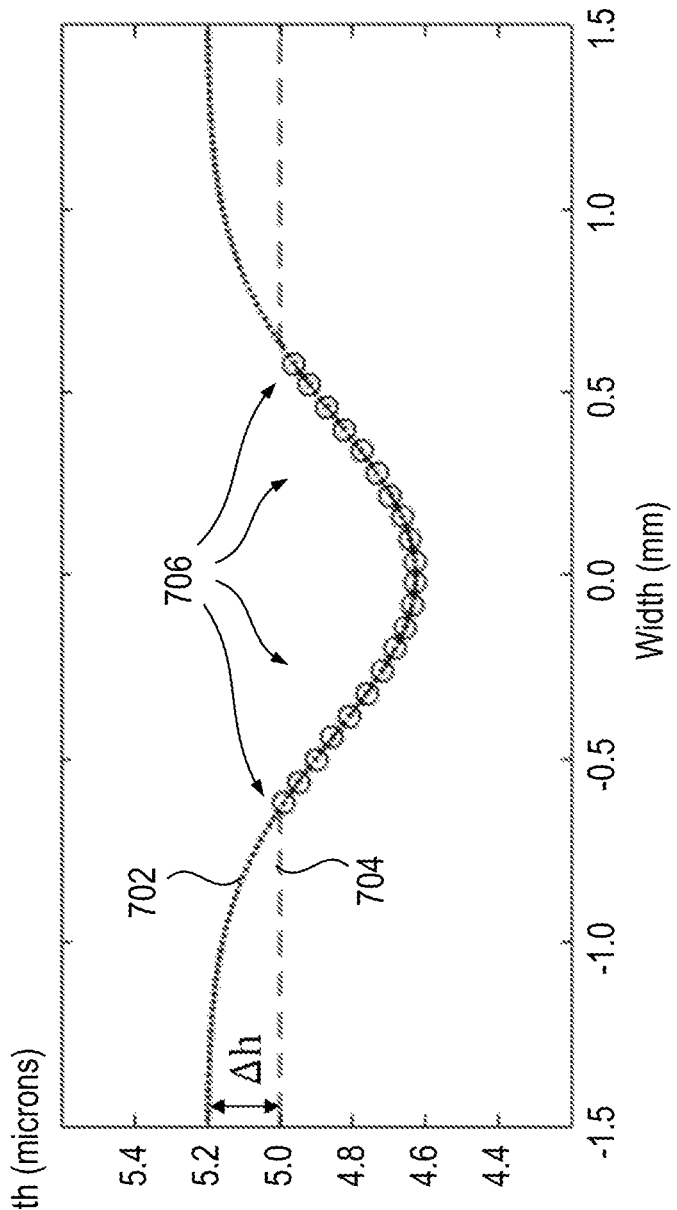
FIG. 7 depicts an example of a representative model fitting in accordance with the illustrative embodiment.

FIG. 7 depicts an example of a representative model fitting in accordance with the illustrative embodiment. Plot 700 shows the relationship between fitted model 702 and measured surface scan 704. Points 706 denote the points used for the fit of the measured data to the model represented by Equation (1).

Values for $\beta$ and $A^*$ can be readily derived via the model fit depicted in plot 700.

Using the values of $\beta$ and $A^*$ determined above, the radiant threshold of the surgical site, $\Phi_{th}$, is calculated based on relative tissue surface heights from the model fit and the actual surgical site, which is given by:

$$\Phi_{th} = (A^* - A)\frac{\beta}{dt} \qquad (2)$$

where A is the initial surface height of the surgical site 116.

At sub-operation 606, using the extracted values for β and $\Phi_{th}$, the model of the formed feature is updated to more accurately represent the ablation properties of surgical site 116. The model, in turn, enables development of a desired path for surgical laser signal 120 through surgical site 116 to more accurately form desired features.

At sub-operation 607, the desired path is planned based upon the updated model.

It should be noted that the sub-method described above is merely one suitable approach for extracting tissue parameters and planning a path for a surgical laser signal through a surgical site. Another suitable sub-method includes planning a desired path based on tissue parameters extracted via analysis of the difference between the surgical site before and after a procedural pass is performed. For example, in some embodiments, a new path is planned based on a comparison of the first intra-procedural scan developed in operation 502 and the second intra-procedural scan developed in operation 507 after the procedural pass performed in operation 506.

Furthermore, in some embodiments, a desired path for the surgical laser signal is generated without employing an automated path planning process and/or extracting tissue parameters. For example, in some embodiments, a desired path is planned based on the difference between the intra-procedural model and the post-procedural goal or specifically designed by the user, such as a surgeon operator who plans the path manually or in semi-automated fashion wherein the path is generated automatically based on information about the tissue at the surgical site that has been gathered and then approved or altered by the surgeon operator.

It should be further noted that sub-methods for extracting tissue parameters for the tissue of a surgical site and planning a procedural path based on those tissue parameters are suitable for use in applications outside the scope of automated or robot-assisted medical procedures. For example, an assessment of tissue parameters at a surgical site can be used to inform a path planned for a manually performed medical procedure, assist a surgeon in selecting the proper laser power, spot size, etc., to employ for a surgical laser signal used to during a procedure, and the like.

Returning now to intra-procedural stage 203, at optional operation 505, the planned path must be approved by a user, such as a surgeon, before moving on to operation 506. If the user does not approve the planned path, intra-procedural stage 203 returns to operation 502 and a new intra-procedural model is developed.

At operation 506, processing circuit 102 steers surgical laser signal 120 (as part of composite signal 126) along the desired path through surgical site 116 to perform a first procedural pass.

At operation 507, a second intra-procedural scan of surgical site 116 is performed, as described above and with respect to operation 501.

At operation 508, the second intra-procedural scan is compared with the post-procedural goal.

If the second intra-procedural scan shows that the post-procedural goal has been satisfactorily achieved, surgery is deemed complete. Typically, a surgical goal is considered achieved if the results are within a pre-defined margin of acceptable error and the surgeon/operator is satisfied with the result.

If, on the other hand, the second intra-procedural scan indicates that the post-procedural goal has not been achieved (e.g., unwanted tissue remains at the surgical site, regions of a tattoo remain untreated, untreated vascular regions remain, etc.), intra-procedural stage 203 returns to operation 502 and operations 502 through 508 are repeated. In some cases, one or more changes are made to the trajectories used to access unwanted tissue when the second surgical procedure is performed.

In some embodiments, each new procedural pass is based on a path that is generated based on the measured results of its preceding procedural pass. In such embodiments, the actual response of the tissue at the surgical site to a known laser signal informs the path planning process. This approach represents a closed-loop process that improves the accuracy with which a complete surgical procedure can be performed and improves the likelihood of procedural success without subjecting the patient to repeated, discontinuous procedures.

Furthermore, the use of surgical planning software in conjunction with surgeon input through GUI 114 enables more accurate positioning of the surgical laser signal as compared with hand-held surgical methods, which reduces collateral tissue damage. It also enables more rapid and precise positioning of the surgical laser energy, which reduces surgical times and increases treatment accuracy, thereby reducing stress on the patient and freeing valuable operating room time for other patients.

In some embodiments, the second intra-procedural scan is compared with the first intra-procedural scan so that the actual tissue response to the first surgical procedure can inform the path planning performed in operation 504. This enables the processing circuit to account for unexpected characteristics of the tissue as manifested during the first surgery.

In some embodiments, a user is afforded oversight of the surgical process through a visual camera feed of the surgical site and tool operation, a digital representation of the surgical site and tool paths, or some combination of supervision modalities.

Figure 8:
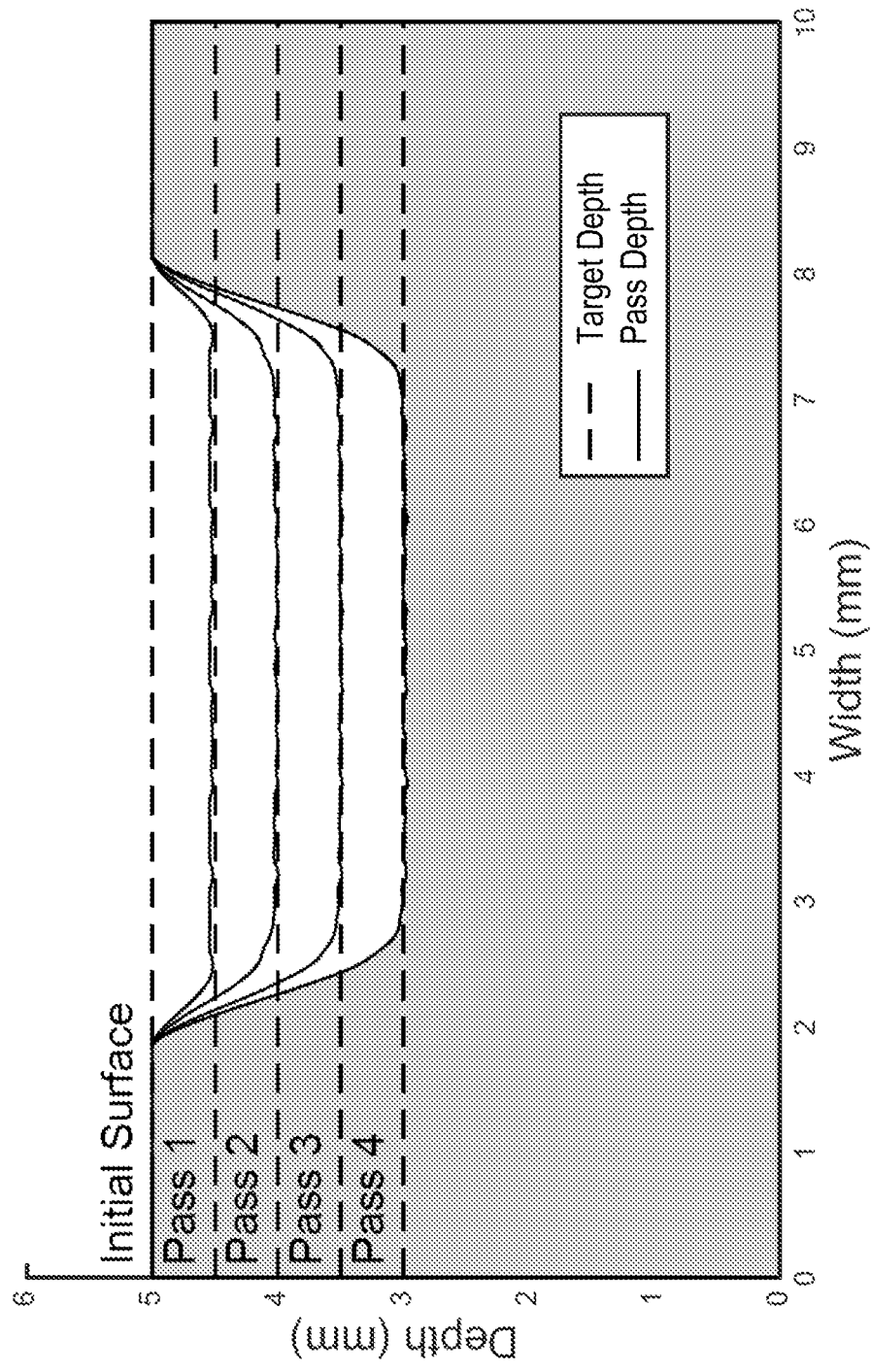
FIG. 8 depict a series of cross sections of planned and realized serial cutting paths through a surgical site, respectively, in accordance with the illustrative embodiment.

FIG. 8 depicts a series of cross sections of planned and realized serial cutting paths through a surgical site, respectively, in accordance with the illustrative embodiment. Each iteration of the surgical plan removes one layer of tissue via a pass of the surgical laser signal along a path.

Model 800 represents a cross section of an exemplary series of planned cutting passes through surgical site 116, where the planned approach includes four passes producing four cuts within a surgical site. The depth of the cut at the surgical site 116 is increased with each cut by approximately 0.5 mm. This illustrates that with each iterative pass, tissue is removed. The specific path, cut dimensions, and pattern shown in FIG. 8 are merely exemplary and any practical treatment region, cutting path, pattern, and cutting dimensions can be used.

Each pass within the series of cutting passes is established for surgical laser signal 120 set to an output continuous wave at a fixed 85% duty cycle, with a power maximal power of 11 W±8% and a $1/e^2$ spot size of approximately 1.75 mm at the surgical site (located approximately 6 inches from the center of beam scanner 112). Continuous velocity control of composite signal 126 is achieved by providing discrete position commands that were closely spaced (0.5 micron) relative to the spot size of the laser signal. In the depicted example, the position commands are updated at a rate of 20 kHz. In the depicted example, each successive cut and laser duty cycle setting is tailored based on the difference between the depth of the intra-operative model of the tissue following the prior cut and the current target depth.

Although the figures show a specific order of method steps, the order of the steps can differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As used herein, the term "circuit" can include hardware structured to execute the functions described herein. In some embodiments, each respective "circuit" can include machine-readable media for configuring the hardware to execute the functions described herein. The circuit can be embodied as one or more circuitry components including, but not limited to, processing circuitry, network interfaces, peripheral devices, input devices, output devices, sensors, etc. In some embodiments, a circuit can take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on).

The "circuit" can also include one or more processors communicably coupled to one or more memory or memory devices. In this regard, the one or more processors can execute instructions stored in the memory or can execute instructions otherwise accessible to the one or more processors. In some embodiments, the one or more processors can be embodied in various ways. The one or more processors can be constructed in a manner sufficient to perform at least the operations described herein. In some embodiments, the one or more processors can be shared by multiple circuits (e.g., circuit A and circuit B can comprise or otherwise share the same processor which, in some example embodiments, can execute instructions stored, or otherwise accessed, via different areas of memory). Alternatively or additionally, the one or more processors can be structured to perform or otherwise execute certain operations independent of one or more co-processors. In other example embodiments, two or more processors can be coupled via a bus to enable independent, parallel, pipelined, or multi-threaded instruction execution. Each processor can be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors can take the form of a single core processor, multi-core processor (e.g., a dual core processor, triple core processor, quad core processor, etc.), microprocessor, etc. In some embodiments, the one or more processors can be external to the apparatus, for example the one or more processors can be a remote processor (e.g., a cloud based processor). Alternatively or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud based server). To that end, a "circuit" as described herein can include components that are distributed across one or more locations. The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A surgical system for manipulating tissue at a surgical site, the system comprising:
   a first laser operative for providing a first laser signal, the first laser signal being operative for manipulating tissue at the surgical site;
   a beam scanner that is configured to controllably direct the first laser signal to points within a first region of the surgical site;
   a surface profiler that is configured to measure a range for points within the first region; and
   a processing circuit that is configured to:
   (1) plan a first path for the first laser signal within the first region, wherein the first path is based on a post-procedural goal and a first estimate of at least one tissue parameter selected from the group consisting of threshold radiant exposure, tissue density, ablation enthalpy, absorption coefficient, optical scattering coefficient, reduced scattering coefficient, refractive index, and scattering anisotropy coefficient, and wherein the first estimate is based on a model of the reaction of the tissue to the laser signal derived from a topological map of a first feature formed at the surgical site using the first laser signal;

(2) control the first laser signal along the first path while simultaneously controlling at least one characteristic of the first laser signal, the at least one characteristic being selected from the group consisting of beam shape, focus, focal depth, spot size, and orientation;

(3) generate a first intra-procedural model of the surgical site based on a measured range for each of a first plurality of points within the first region, wherein the range for each point of the first plurality thereof is measured after the first laser signal has traversed the first path; and (4) perform a first comparison of the post-procedural goal and the first intra-procedural model.

2. The system of claim 1 wherein the processing circuit is further configured to:

(5) plan a second path for the first laser signal within the first region based on the first comparison;

(6) control the first laser signal along the second path;

(7) generate a second intra-procedural model of the surgical site based on a measured range for each of a second plurality of points within the first region, wherein the range for each point of the second plurality thereof is measured after the first laser signal is controlled along the second path; and (8) perform a second comparison of the post-procedural goal and the second intra-procedural model.

3. The system of claim 2 wherein the processing circuit is further configured to:

(9) generate a second estimate of the at least one tissue parameter based on a difference between the first intra-procedural model and a third intra-procedural model that is based on a measured range for each of a third plurality of points within the first region, wherein the range for each point of the third plurality thereof is measured before the first laser signal is controlled along the first path; and

(10) plan the second path such that it is further based on the second estimate.

4. The system of claim 1 wherein the processing circuit is further configured to (5) generate the first estimate such that it is based on an interaction between the first laser signal and a first point within the first region.

5. The system of claim 1 wherein the post-procedural goal is based on a second intra-procedural model of the surgical site, wherein the second intra-procedural model is based on a measured range for each of a second plurality of points within the first region, the range for each point of the second plurality thereof being measured before the first laser signal is controlled along the first path.

6. The system of claim 1 wherein the post-procedural goal is based on a first image of the surgical site, wherein the first image is a three-dimensional (3D) image taken before the first laser signal is controlled along the first path.

7. The system of claim 1 further comprising a second laser operative for providing a second laser signal, wherein the beam scanner is configured to controllably direct the second laser signal to any point within the first region.

8. The system of claim 7 wherein the surface profiler includes the second laser.

9. The system of claim 8 wherein the surface profiler includes a laser triangulation sensor, the laser triangulation sensor including the second laser.

10. The system of claim 1 wherein the beam scanner comprises a two-axis galvanometer.

11. The system of claim 1 wherein the beam scanner comprises a two-axis MEMS mirror.

12. The system of claim 1 further comprising a graphical user interface (GUI) that enables a user to specify a classification for tissue in at least one region of the surgical site.

13. A method for manipulating tissue at a surgical site, the method comprising:

generating a model of the reaction of the tissue to the laser signal from a topological map of a first feature formed at the surgical site using the first laser signal;

generating a first estimate of at least one tissue parameter based on the model, the at least one tissue parameter being selected from the group consisting of threshold radiant exposure, tissue density, ablation enthalpy, absorption coefficient, optical scattering coefficient, reduced scattering coefficient, refractive index, and scattering anisotropy coefficient;

planning a first path for the first laser signal within a first region of a surgical site, wherein the first path is based on a post-procedural goal and the first estimate;

controlling at least one characteristic of the first laser signal, the at least one characteristic being selected from the group consisting of beam shape, focus, focal depth, spot size, and orientation;

generating a first intra-procedural model of the surgical site based on a measured range for each of a first plurality of points within the first region, wherein the range for each point of the first plurality thereof is measured after the first laser signal has traversed the first path; and performing a first comparison of the post-procedural goal and the first intra-procedural model.

14. The method of claim 13 further comprising:

planning a second path for the first laser signal within the first region, wherein the second path is based on the first comparison;

controlling the first laser signal along the second path;

generating a second intra-procedural model of the surgical site based on a measured range for each of a second plurality of points within the first region, wherein the range for each point of the second plurality thereof is measured after the first laser signal is directed along the second path; and performing a second comparison of the post-procedural goal and the second intra-procedural model.

15. The method of claim 14 further comprising:

generating a second estimate of the at least one tissue parameter based on a difference between the second intra-procedural model and a third intra-procedural model that is based on a measured range for each of a third plurality of points within the first region, wherein the range for each point of the third plurality thereof is measured before the first laser signal is directed along the first path; and planning the second path such that it is further based on the at least one tissue parameter and the second estimate.

16. The method of claim 13 further comprising:

controlling the first laser signal to create the first feature; and generating the first estimate based on the first feature and a model of the first feature.

17. The method of claim 13 further comprising measuring the range for each of the first plurality of points, wherein the range is measured via a laser triangulation sensor.

18. The method of claim 13 wherein the first laser signal is controlled along the first path by a two-axis beam scanner.

19. The method of claim 18 wherein the beam scanner comprises a two-axis galvanometer.

20. The method of claim 18 wherein the beam scanner comprises a two-axis MEMS mirror.

21. The method of claim 13 wherein the post-procedural goal is generated by operations comprising:
   generating a first pre-procedural model based on a first image of the surgical site, the first pre-procedural model being a 3D model, and the first image being generated before the first laser signal is controlled along the first path; and
   specifying a first classification for at least one region within the first pre-procedural model.

22. The method of claim 21 wherein the post-procedural goal is generated by operations further comprising:
   generating a first surface scan of the first region, the first surface scan being based on a range for each of a second plurality of points measured before the first laser signal is controlled along the first path; and
   adapting the first pre-procedural model based on the first surface scan.

* * * * *